US010150775B2

United States Patent
Pasternak et al.

(10) Patent No.: US 10,150,775 B2
(45) Date of Patent: *Dec. 11, 2018

(54) 6-AMIDO DERIVATIVES OF 4,5A-EPOXYMORPHINANS FOR TREATMENT OF PAIN

(71) Applicant: Sloan-Kettering Institute for Cancer Research, New York, NY (US)

(72) Inventors: Gavril Pasternak, New York, NY (US); Susruta Majumdar, Stamford, CT (US)

(73) Assignee: Sloan-Kettering Institute for Cancer Research, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/672,245

(22) Filed: Aug. 8, 2017

(65) Prior Publication Data

US 2018/0057504 A1    Mar. 1, 2018

Related U.S. Application Data

(63) Continuation of application No. 14/281,237, filed on May 19, 2014, now Pat. No. 9,725,457, which is a continuation of application No. 13/879,908, filed as application No. PCT/US2011/056827 on Oct. 19, 2011, now abandoned.

(60) Provisional application No. 61/394,481, filed on Oct. 19, 2010.

(51) Int. Cl.
*A61K 51/04* (2006.01)
*C07D 489/08* (2006.01)
*G01N 33/94* (2006.01)

(52) U.S. Cl.
CPC ........ *C07D 489/08* (2013.01); *A61K 51/0455* (2013.01); *G01N 33/9486* (2013.01)

(58) Field of Classification Search
CPC .......................... A61K 51/0455; C07D 489/08
USPC ................................................. 552/610, 612
See application file for complete search history.

(56) References Cited

U.S. PATENT DOCUMENTS

| | | | |
|---|---|---|---|
| 5,739,145 A | 4/1998 | Nagase et al. | |
| 5,834,478 A * | 11/1998 | Ito | C07D 489/08 514/282 |
| 6,147,084 A | 11/2000 | Nagase et al. | |
| 6,177,438 B1 * | 1/2001 | Nagase | C07D 489/00 514/280 |
| 6,323,212 B1 | 11/2001 | Nagase et al. | |
| 6,583,151 B2 * | 6/2003 | Nagase | A61K 31/485 514/289 |
| 8,338,442 B2 | 12/2012 | Kumagai et al. | |
| 8,420,662 B2 * | 4/2013 | Takaki | A61K 9/2009 424/400 |
| 8,481,501 B2 * | 7/2013 | Cashman | C07D 489/00 514/24 |
| 8,637,539 B2 * | 1/2014 | Nagase | A61K 31/4745 514/282 |
| 8,778,958 B2 * | 7/2014 | Cashman | C07D 498/08 514/282 |
| 8,796,301 B2 * | 8/2014 | Ikeda | C07D 489/08 514/282 |
| 8,829,019 B2 * | 9/2014 | Ohta | A61K 9/2009 424/400 |
| 9,006,262 B2 * | 4/2015 | Suzuki | A61K 31/485 514/289 |
| 9,725,457 B2 | 8/2017 | Pasternak et al. | |
| 2004/0116456 A1 | 6/2004 | Kumagai et al. | |
| 2008/0234307 A1 | 9/2008 | Schuetz et al. | |
| 2009/0041687 A1 | 2/2009 | Beumer et al. | |
| 2009/0325857 A1 | 12/2009 | Beumer et al. | |
| 2010/0120815 A1 | 5/2010 | Takaki et al. | |
| 2010/0130524 A1 | 5/2010 | Ikeda et al. | |
| 2010/0190728 A1 | 7/2010 | Cashman et al. | |
| 2010/0222309 A1 | 9/2010 | Ona et al. | |
| 2011/0263630 A1 | 10/2011 | Cashman | |

(Continued)

FOREIGN PATENT DOCUMENTS

EP          1762569 A1      3/2007
JP       2009507872 A       2/2009

(Continued)

OTHER PUBLICATIONS

International Preliminary Report on Patentability for Application No. PCT/US2011/056827, dated Apr. 23, 2013.

(Continued)

*Primary Examiner* — Sabiha N Qazi
(74) *Attorney, Agent, or Firm* — Wolf, Greenfield & Sacks, P.C.

(57) ABSTRACT

Compounds of formula:

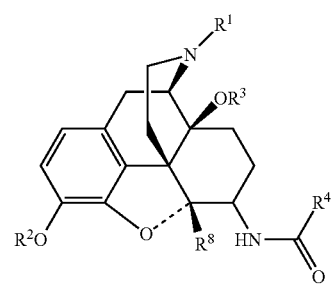

in which $R^4$ is chosen from substituted phenyl, optionally substituted naphthylene, optionally substituted anthracene and optionally substituted aromatic heterocycle, are useful as analgesics.

20 Claims, No Drawings

(56) References Cited

U.S. PATENT DOCUMENTS

| 2012/0114752 A1* | 5/2012 | Ohta | A61K 9/2009 |
| | | | 424/465 |
| 2012/0302590 A1 | 11/2012 | Bhide et al. | |
| 2013/0203797 A1* | 8/2013 | Kobayashi | A61K 31/485 |
| | | | 514/282 |
| 2013/0289060 A1 | 10/2013 | Pasternak et al. | |
| 2013/0289061 A1 | 10/2013 | Bhide et al. | |
| 2013/0310414 A1* | 11/2013 | Suzuki | A61K 31/485 |
| | | | 514/282 |
| 2014/0255308 A1 | 9/2014 | Pasternak et al. | |

FOREIGN PATENT DOCUMENTS

| WO | WO 2001/68080 A2 | 9/2001 |
| WO | WO 2005/117589 A1 | 12/2005 |
| WO | WO 2010/006119 A1 | 1/2010 |
| WO | WO 2010/083384 A2 | 7/2010 |

OTHER PUBLICATIONS

International Search Report for PCT/US2011/056827 dated May 17, 2012.

Supplementary European Search Report for Application No. EP 11835042.0, dated Mar. 28, 2014.

Clark et al., Kappa opiate receptor multiplicity: evidence for two U50,488-sensitive kappa 1 subtypes and a novel kappa 3 subtype. J Pharmacol Exp Ther. Nov. 1989;251(2):461-8.

D'Amour, A Method for Determining Loss of Pain Sensation. J Pharmacol Exp Ther. May 1941;72(1):74-9.

Ghirmai et al. Synthesis and Biological Evaluation of .alpha. and .beta.-6-Amido Derivatives of 17-cyclopropylmethyl-3, 14 .beta.-dihydroxy-4 5.alpha.-epoxymorphinan: Potential Alcohol-Cessation. J. Med. Chem., 51, pp. 1913-1924 (2008).

Ghirmai et al. Synthesis and Pharmacological Evaluation of 6-naltrexamine Analogs or Alcohol Sessation. Biorganic and Medicinal Chemistry, vol. 17, pp. 6671-6681 (2009).

Gistrak et al., Pharmacological actions of a novel mixed opiate agonist/antagonist: naloxone benzoylhydrazone. J Pharmacol Exp Ther. Nov. 1989;251(2):469-76.

Jiang et al., Stereochemical studies on medicinal agents. 23. Synthesis and biological evaluation of 6-amino derivatives of naloxone and naltrexone. J Med Chem. Aug. 1977;20(8):1100-2.

Li et al., Design, synthesis, and biological evaluation of 6alpha- and 6beta-N-heterocyclic substituted naltrexamine derivatives as mu opioid receptor selective antagonists. J Med Chem. Mar. 12, 2009;52(5):1416-27. doi: 10.1021/jm801272c. Epub Jun. 4, 2010. 31 pages.

Majumdar et al., Generation of novel radiolabeled opiates through site-selective iodination. Bioorg Med Chem Lett. Jul. 1, 2011;21(13):4001-4. doi: 10.1016/j.bmcl.2011.05.008. Epub Jul. 1, 2012. 11 pages.

Paul et al., Differential blockade by naloxonazine of two mu opiate actions: analgesia and inhibition of gastrointestinal transit. Eur J Pharmacol. May 10, 1988;149(3):403-4.

Rothman et al., Interaction of endogenous opioid peptides and other drugs with four kappa opioid binding sites in guinea pig brain. Peptides. Mar.-Apr. 1990;11(2):311-31.

Zhang et al., Specific cross-linking of Lys233 and Cys235 in the mu opioid receptor by a reporter affinity label. Biochemistry. Feb. 22, 2005;44(7):2271-5.

\* cited by examiner

6-AMIDO DERIVATIVES OF 4,5A-EPOXYMORPHINANS FOR TREATMENT OF PAIN

CROSS REFERENCE TO RELATED APPLICATIONS

This application is a continuation of U.S. patent application Ser. No. 14/281,237, filed May 19, 2014 and issued as U.S. Pat. No. 9,725,457, which is a continuation of U.S. patent application Ser. No. 13/879,908, filed Apr. 17, 2013, which is a national phase filing under 35 U.S.C. § 371 of PCT International Application PCT/US2011/056827, filed Oct. 19, 2011, and published under PCT Article 21(2) in English as WO 2012/054566 on Apr. 26, 2012, which claims priority to U.S. provisional application 61/394,481, filed Oct. 19, 2010. The entire contents of all the applications above are incorporated herein by reference.

GOVERNMENT SUPPORT

This invention was made with government support under grant numbers DA000220, DA002615, and DA006241 awarded by the National Institutes of Health. The government has certain rights in the invention.

FIELD OF THE INVENTION

The invention relates to opioid receptor binding 6-amido derivatives of 4,5a-epoxymorphinans. The compounds are useful as analgesics.

BACKGROUND OF THE INVENTION

Opiates have been the subject of intense research since the isolation of morphine in 1805, and thousands of compounds having opiate or opiate-like activity have been identified. Many opioid receptor-interactive compounds, including those used for producing analgesia (e.g., morphine) and those used for treating drug addiction (e.g., methadone, buprenorphine and naltrexone) in humans work by triggering μ opioid receptors in the central nervous system (CNS) and by crossing the blood-brain barrier. However, as there are μ opioid receptors outside the CNS, these opiates usually cause unwanted peripheral side effects. Often, the peripheral side effects manifest themselves in the gastrointestinal (GI) tract and the respiratory system. For instance, prolonged morphine administration often causes constipation, and prolonged morphine administration ultimately causes life-threatening respiratory depression in patients. Other side effects appear to arise from the central action of morphine-like compounds. These central side effects of μ ligands include physical dependence (addiction) and sedation. Thus, a drug that is able to treat symptoms of pain, but not cause some or all of the peripheral and central side effects, would be most valuable.

SUMMARY OF THE INVENTION

The compounds of the invention are useful as analgesics having lessened liability for constipation and respiratory depression.

In one aspect, the invention relates to compounds of formula I:

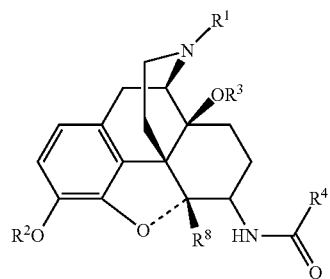

wherein $R^1$ is chosen from (a) $C_2$-$C_{10}$ hydrocarbon other than cyclopropylmethyl; and (b) —$CH_2$—Het, wherein Het is a five- or six-membered heterocycle;

$R^2$ is chosen from hydrogen, ($C_1$-$C_6$)acyl, ($C_1$-$C_6$)oxaalkyl, and ($C_1$-$C_6$)acyloxaalky;

$R^3$ is chosen from hydrogen and ($C_1$-$C_6$)alkyl;

$R^4$ is chosen from (a) phenyl substituted at other than 2 or 6 with from one to three substituents chosen from amino, bromo, chloro, iodo, hydroxy, nitro, cyano, ($C_1$-$C_3$)alkyl, ($C_1$-$C_3$)haloalkyl, ($C_1$-$C_3$)haloalkoxy, ($C_1$-$C_3$)alkoxy and $R^{10}$;

(b) optionally substituted naphthylene;

(c) optionally substituted anthracene;

(d) optionally substituted aromatic heterocycle;

$R^8$ is chosen from hydrogen and ($C_1$-$C_6$)alkyl;

$R^{10}$ is optionally substituted phenyl, optionally substituted aromatic heterocycle or optionally substituted non-aromatic oxygen or sulfur heterocycle;

wherein the substituents on naphthylene, anthracene, heterocycle or $R^{10}$ are chosen independently from halogen, hydroxy, nitro, cyano, ($C_1$-$C_3$)alkyl, ($C_1$-$C_3$)haloalkyl, ($C_1$-$C_3$)haloalkoxy, ($C_1$-$C_3$)acyl and ($C_1$-$C_3$)alkoxy.

In another aspect, the invention relates to a compound of formula II:

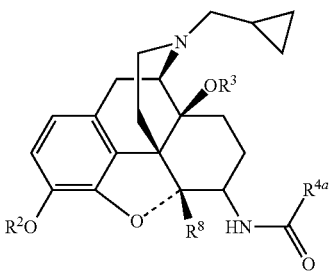

wherein
R⁴ᵃ is chosen from

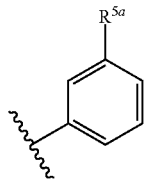
(a)

wherein $R^{5a}$ is chosen from bromo, chloro, iodo, cyano, $(C_1-C_3)$alkyl, $(C_1-C_3)$haloalkyl, $(C_1-C_3)$haloalkoxy, $(C_2-C_3)$alkoxy and $R^{10}$;

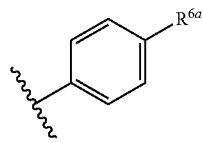
(b)

wherein $R^{6a}$ is chosen from hydroxy, nitro, cyano, $(C_2-C_3)$haloalkyl, $(C_1-C_3)$haloalkoxy, $(C_1-C_3)$alkoxy and $R^{10}$;

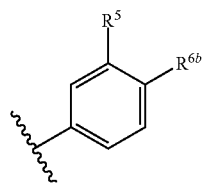
(c)

wherein $R^5$ is chosen from halogen, hydroxy, nitro, cyano, $(C_1-C_3)$alkyl, $(C_1-C_3)$haloalkyl, $(C_1-C_3)$haloalkoxy, $(C_1-C_3)$alkoxy and $R^{10}$; and $R^{6b}$ is chosen from halogen, hydroxy, nitro, cyano, $(C_1-C_3)$alkyl, $(C_1-C_3)$haloalkyl, $(C_1-C_3)$haloalkoxy, $(C_1-C_3)$alkoxy and $R^{10}$, or, taken together, $R^5$ and $R^{6b}$ are alkylenedioxy, with the proviso that both $R^5$ and $R^{6b}$ are not chloro or fluoro;

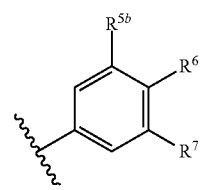
(d)

wherein $R^{5b}$ is chosen from bromo, chloro, iodo, hydroxy, nitro, cyano, $(C_1-C_3)$alkyl, $(C_1-C_3)$haloalkyl, $(C_1-C_3)$haloalkoxy, $(C_1-C_3)$alkoxy and $R^{10}$; $R^6$ is chosen from hydrogen, halogen, hydroxy, nitro, cyano, $(C_1-C_3)$alkyl, $(C_1-C_3)$haloalkyl, $(C_1-C_3)$haloalkoxy, $(C_1-C_3)$alkoxy and $R^{10}$; $R^7$ is chosen from halogen, hydroxy, nitro, cyano, $(C_1-C_3)$alkyl, $(C_1-C_3)$haloalkyl, $(C_1-C_3)$haloalkoxy, $(C_1-C_3)$alkoxy and $R^{10}$; and (e) napthylene substituted with from one to three substituents chosen from halogen, hydroxy, nitro, cyano, $(C_1-C_3)$alkyl, $(C_1-C_3)$haloalkyl, $(C_1-C_3)$haloalkoxy, $(C_1-C_3)$alkoxy and $R^{10}$;

(f) anthracene optionally substituted with from one to three substituents chosen from halogen, hydroxy, nitro, cyano, $(C_1-C_3)$alkyl, $(C_1-C_3)$haloalkyl, $(C_1-C_3)$haloalkoxy, $(C_1-C_3)$alkoxy and $R^{10}$;

(g) aromatic heterocycle other than unsubstituted pyridine, quinoline or isoquinoline, optionally substituted with from one to three substituents chosen from halogen, hydroxy, nitro, cyano, $(C_1-C_3)$alkyl, $(C_1-C_3)$haloalkyl, $(C_1-C_3)$haloalkoxy, $(C_1-C_3)$alkoxy and $R^{10}$.

In another aspect, the invention relates to a pharmaceutical composition comprising at least one compound of the formula above and a pharmaceutically acceptable carrier.

In another aspect, the invention relates to a method for reducing pain comprising administering to a subject suffering from pain an amount of a compound described above effective to reduce pain.

DETAILED DESCRIPTION OF THE INVENTION

Analgesic compounds of the invention fall into two primary classes: compounds of general formula II, in which $R^1$ is cyclopropylmethyl, and compounds of general formula I, in which $R^1$ is not cyclopropylmethyl. The compounds of general formula I include a series in which $R^1$ is allyl and one in which $R^1$ is cyclobutylmethyl. When $R^1$ is —CH₂—Het, Het may be tetrahydrofuranyl.

In one aspect, the invention relates to compounds of formula I:

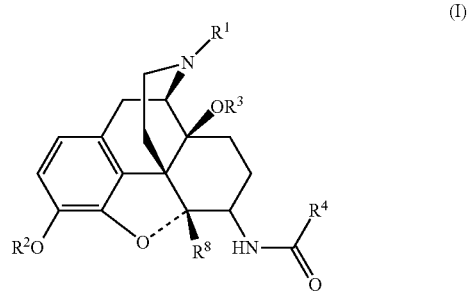
(I)

Some embodiments of the invention can be represented by the formula:

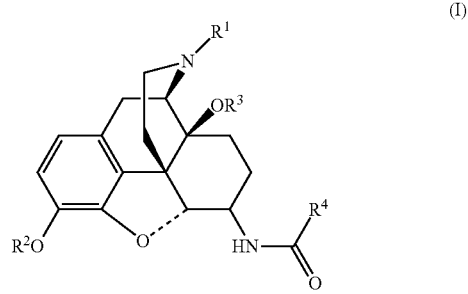
(I)

which is a subset of formula I. In these compounds, $R^1$ is cyclobutylmethyl or allyl;

$R^2$ is chosen from hydrogen, $(C_1-C_6)$acyl, $(C_1-C_6)$oxaalkyl, and $(C_1-C_6)$acyloxaalky;

$R^3$ is hydrogen or methyl;

$R^4$ is chosen from (a) phenyl substituted at other than 2 or 6 with from one to three substituents chosen from bromo, chloro, iodo, hydroxy, nitro, cyano, $(C_1-C_3)$alkyl, $(C_1-C_3)$haloalkyl, $(C_1-C_3)$haloalkoxy, $(C_1-C_3)$alkoxy and $R^{10}$;

(b) optionally substituted naphthylene;

(c) optionally substituted anthracene;

(d) aromatic heterocycle chosen from pyridine, thiophene, furan and pyrrole optionally substituted with from one to three substituents chosen from bromo, chloro, iodo, hydroxy, nitro, cyano, $(C_1-C_3)$alkyl, $(C_1-C_3)$haloalkyl, $(C_1-C_3)$haloalkoxy and $(C_1-C_3)$alkoxy;

$R^8$ is hydrogen; and $R^{10}$ is optionally substituted phenyl, optionally substituted aromatic heterocycle or optionally substituted non-aromatic oxygen or sulfur heterocycle;

wherein the substituents on naphthylene, anthracene, heterocycle or $R^{10}$ are chosen independently from halogen, hydroxy, nitro, cyano, $(C_1-C_3)$haloalkyl, $(C_1-C_3)$alkyl, $(C_1-C_3)$acyl and $(C_1-C_3)$alkoxy.

In some embodiments of the compounds of formula II, $R^{4a}$ is (g), an aromatic heterocycle other than unsubstituted pyridine, quinoline or isoquinoline, optionally substituted with from one to three substituents chosen from halogen, hydroxy, nitro, cyano, $(C_1-C_3)$alkyl, $(C_1-C_3)$haloalkyl, $(C_1-C_3)$haloalkoxy, $(C_1-C_3)$alkoxy and $R^{10}$. In these embodiments $R^{4a}$ may also be other than pyridine monosubstituted with bromine, chlorine, methyl, methoxy or cyano. In these embodiments $R^{4a}$ may also be other than unsubstituted pyrimidine, cinnoline quinazoline or pyridazine.

In some embodiments, the amide substituent at the oxymorphone 6 position is in the β configuration and $R^8$ is hydrogen:

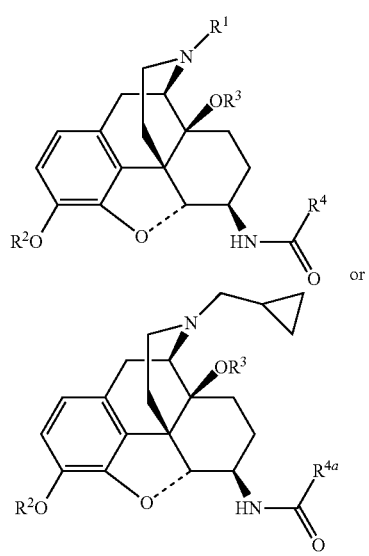

In some embodiments $R^2$ is hydrogen; in others $R^2$ is chosen from $CH_3$, acetyl, acetoxymethyl, $-CH_2OC(=O)C(CH_3)_3$ and $-CH_2OC(=O)OCH_3$.

In some embodiments, $R^3$ is hydrogen; in others $R^3$ is methyl.

In some embodiments, $R^4$ or $R^{4a}$ is

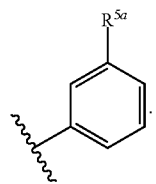

In some of these embodiments, $R^{5a}$ is chosen from bromo, chloro, iodo, $(C_1-C_3)$haloalkyl, $(C_1-C_3)$haloalkoxy, $(C_2-C_3)$alkoxy and $R^{10}$. In narrower embodiments, $R^{5a}$ is chosen from bromo, chloro, iodo, trifluoromethyl, trifluoromethoxy and $R^{10}$, and $R^{10}$ is chosen from phenyl, furanyl and thiophenyl optionally substituted with one to three substituents independently chosen from halogen, methyl, trifluoromethyl, methoxy, trifluoromethoxy, methylenedioxy and acetyl. In some embodiments $R^{5a}$ is iodo, either in its normal isotopic ratio or in a ratio enriched in $^{125}I$. In other embodiments, $R^4$ or $R^{4a}$ is

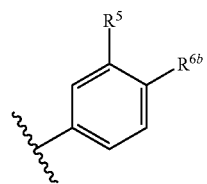

wherein $R^5$ is chosen from halogen, nitro, cyano, methyl, trifluoromethyl, trifluoromethoxy, methoxy, phenyl, thiophenyl, furanyl; and $R^{6b}$ is chosen from halogen, nitro, cyano, methyl, trifluoromethyl, trifluoromethoxy, methoxy, phenyl, thiophenyl and furanyl. In one embodiment, $R^4$ or $R^{4a}$ is 3,4-diiodophenyl, which also may be enriched in $^{125}I$.

In one embodiment, the amide substituent at the oxymorphone 6 position is in the β configuration and $R^4$ is phenyl substituted at other than 2 or 6 with from one to three substituents chosen from bromo, chloro, iodo, hydroxy, nitro, cyano, $(C_1-C_3)$alkyl, $(C_1-C_3)$haloalkyl, $(C_1-C_3)$haloalkoxy, $(C_1-C_3)$alkoxy and $R^{10}$. In a narrower embodiment, $R^1$ is cyclobutylmethyl or allyl; $R^3$ is hydrogen or methyl; $R^8$ is hydrogen; the amide substituent at the oxymorphone 6 position is in the β configuration and $R^4$ is phenyl substituted at other than 2 or 6 with from one to three substituents chosen from bromo, chloro, iodo, hydroxy, nitro, cyano, $(C_1-C_3)$alkyl, $(C_1-C_3)$haloalkyl, $(C_1-C_3)$haloalkoxy, $(C_1-C_3)$alkoxy and $R^{10}$. A preferred subgenus is that in which $R^4$ is phenyl substituted at the 3- and 4-positions with two substituents chosen independently from bromo, chloro, iodo, methyl, trifluoromethyl, methoxy and trifluoromethoxy. An example is the compound in which $R^1$ is allyl; $R^2$ is H; $R^3$ and $R^8$ are hydrogen and $R^4$ is 3,4-diiodophenyl. In another preferred subgenus, $R^4$ is phenyl substituted at the 3- or 4-position with a substituent chosen from bromo, chloro, iodo, methyl, trifluoromethyl, methoxy, trifluoromethoxy and $R^{10}$. $R^{10}$ may be chosen from phenyl, furanyl and thiophenyl optionally substituted with one to three substituents independently chosen from halogen, methyl, trifluoromethyl, methoxy, trifluoromethoxy, methylenedioxy and acetyl. In general, it appears that compounds in which $R^1$ is substituted phenyl do not exhibit useful analgesic activity when the substituents are at 2 and/or 6.

In another embodiment, the amide substituent at the oxymorphone 6 position is in the β configuration and $R^4$ is optionally substituted quinoline. In some embodiments, $R^1$ is allyl; $R^2$ is H; $R^3$ and $R^8$ are hydrogen and $R^4$ is optionally substituted quinoline.

As described above, $R^8$ is chosen from hydrogen and $(C_1-C_6)$alkyl. Preferred compounds are those in which $R^8$ is hydrogen or methyl.

Pharmaceutical compositions in accord with the invention comprise a pharmaceutically acceptable carrier and a compound as described above.

The compounds described above may be employed in a method for reducing pain. The method comprises administering to a subject suffering from pain an amount of a compound above effective to reduce pain. In the treatment of pain, the pain may be reduced without substantial reduction of intestinal motility and/or without substantial respiratory depression. The term "substantial" is intended to mean that the intestinal motility or respiration rate is reduced by at least 50% at a dose that is the analgesic $ED_{50}$ for a naïve subject. The compounds may also be employed in a method for reducing pain in a μ-opioid-dependent patient. The compounds may also be employed in assays for the kappa3 receptor; radioiodinated compounds are particularly useful for this assay.

DEFINITIONS

Throughout this specification the terms and substituents retain their definitions.

Alkyl is intended to include linear or branched, or cyclic hydrocarbon structures and combinations thereof. A combination would be, for example, cyclopropylmethyl. Lower alkyl refers to alkyl groups of from 1 to 6 carbon atoms. Examples of lower alkyl groups include methyl, ethyl, propyl, isopropyl, cyclopropyl, butyl, s- and t-butyl, cyclobutyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

Alkoxy or alkoxyl refers to groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole. As used herein aryl and heteroaryl refer to residues in which one or more rings are aromatic, but not all need be.

Arylalkyl means an aryl ring attached to an alkyl residue in which the point of attachment to the parent structure is through the alkyl. Examples are benzyl, phenethyl and the like. Heteroarylalkyl means an alkyl residue attached to a heteroaryl ring. Examples include, e.g., pyridinylmethyl, pyrimidinylethyl and the like.

$C_2$ to $C_{10}$ hydrocarbon means a linear, branched, or cyclic residue comprised of hydrogen and carbon as the only elemental constituents and includes alkyl, cycloalkyl, polycycloalkyl, alkenyl, alkynyl, aryl and combinations thereof. Examples include benzyl, phenethyl, cyclohexylmethyl, cyclopropylmethyl, cyclobutylmethyl, allyl, camphoryl and naphthylethyl.

Unless otherwise specified, the term "carbocycle" is intended to include ring systems in which the ring atoms are all carbon but of any oxidation state. Thus $(C_3-C_{10})$ carbocycle refers to both non-aromatic and aromatic systems, including such systems as cyclopropane, benzene and cyclohexene; $(C_8-C_{12})$ carbopolycycle refers to such systems as norbornane, decalin, indane and naphthalene. Carbocycle, if not otherwise limited, refers to monocycles, bicycles and polycycles.

Heterocycle means a cycloalkyl or aryl residue in which one to two of the carbons is replaced by a heteroatom such as oxygen, nitrogen or sulfur. Heteroaryls form a subset of heterocycles. Examples of heterocycles include pyrrolidine, pyrazole, pyrrole, imidazole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, pyrazine, thiophene, furan, oxazole, oxazoline, isoxazole, dioxane, tetrahydrofuran and the like.

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxyloweralkyl, carbonyl, phenyl, heteroaryl, benzenesulfonyl, hydroxy, loweralkoxy, haloalkoxy, oxaalkyl, carboxy, alkoxycarbonyl [—C(=O)O-alkyl], alkoxycarbonylamino [HNC(=O)O-alkyl], carboxamido [—C(=O)NH$_2$], alkylaminocarbonyl [—C(=O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2 or 3 hydrogen atoms are replaced with a specified radical. In the case of alkyl and cycloalkyl, more than three hydrogen atoms can be replaced by fluorine; indeed, all available hydrogen atoms could be replaced by fluorine.

The compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, as well as their racemic and optically pure forms. It will be apparent that certain chiral centers are specified in compounds set forth in the claims. In these cases, the chiral centers that are not specified encompass both configurations;

those that are specified encompass only the specified configuration. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, and as would be understood by the person of skill in the art, the recitation of "a compound"—unless expressly further limited—is intended to include salts of that compound. In a particular embodiment, the term "compound of formula I" refers to the compound or a pharmaceutically acceptable salt thereof.

The compounds of the invention may exist as salts, i.e. cationic species. The term "pharmaceutically acceptable salt" refers to salts whose counter ion (anion) derives from pharmaceutically acceptable non-toxic acids including inorganic acids and organic acids. Suitable pharmaceutically acceptable acids for salts of the compounds of the present invention include, for example, acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like.

It will be recognized that the compounds of this invention can exist in radiolabeled form, i.e., the compounds may contain one or more atoms containing an atomic mass or mass number different from the atomic mass or mass number usually found in nature. Alternatively, a plurality of molecules of a single structure may include at least one atom that occurs in an isotopic ratio that is different from the isotopic ratio found in nature. Radioisotopes of hydrogen, carbon, phosphorous, fluorine, chlorine and iodine include $^{2}H$, $^{3}H$, $^{11}C$, $^{13}C$, $^{14}C$, $^{15}N$, $^{35}S$, $^{18}F$, $^{36}Cl$, $^{125}I$, $^{124}I$ and $^{131}I$ respectively. Compounds that contain those radioisotopes and/or other radioisotopes of other atoms are within the scope of this invention. Tritiated, i.e. $^{3}H$, and carbon-14, i.e., $^{14}C$, radioisotopes are particularly preferred for their ease in preparation and detectability. Compounds that contain isotopes $^{11}C$, $^{13}N$, $^{15}O$, $^{124}I$ and $^{18}F$ are well suited for positron emission tomography. Radiolabeled compounds of formulae I and II of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

Although this invention is susceptible to embodiment in many different forms, preferred embodiments of the invention are shown. It should be understood, however, that the present disclosure is to be considered as an exemplification of the principles of this invention and is not intended to limit the invention to the embodiments illustrated. It may be found upon examination that certain members of the claimed genus are not patentable to the inventors in this application. In this event, subsequent exclusions of species from the compass of applicants' claims are to be considered artifacts of patent prosecution and not reflective of the inventors' concept or description of their invention; the invention encompasses all of the members of the genera I and II that are not already in the possession of the public.

While it may be possible for the compounds of formula I or II to be administered as the raw chemical, it is preferable to present them as a pharmaceutical composition. According to a further aspect, the present invention provides a pharmaceutical composition comprising a compound of formula I or II or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof. The compositions may be formulated for oral, topical or parenteral administration. For example, they may be given intravenously, intraarterially, subcutaneously, and directly into the CNS—either intrathecally or intracerebroventricularly.

Formulations include those suitable for oral, parenteral (including subcutaneous, intradermal, intramuscular, intravenous and intraarticular), rectal and topical (including dermal, buccal, sublingual and intraocular) administration. The compounds are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity. The formulations may conveniently be presented in unit dosage form and may be prepared by any of the methods well known in the art of pharmacy. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose or multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological systems associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological systems of a disease, even though a diagnosis of this disease may not have been made.

ABBREVIATIONS

The following abbreviations and terms have the indicated meanings throughout:
Ac=acetyl
Boc=t-butyloxy carbonyl
BOP=benzotriazol-1-yloxy-tris(dimethylamino)phosphonium hexafluorophosphate
Bu=butyl
c-=cyclo
DCM=dichloromethane=methylene chloride=$CH_2Cl_2$
DIEA=diisopropylethylamine
DMF=N,N-dimethylformamide
DMSO=dimethyl sulfoxide
DOR=delta opioid receptor
EtOAc=ethyl acetate
EtOH=ethanol
GC=gas chromatography
HOAc=acetic acid
KOR=kappa opioid receptor
Me=methyl
MOR=mu opioid receptor
MTBE=methyl t-butyl ether
PEG=polyethylene glycol
Ph=phenyl
PhOH=phenol
rt=room temperature
sat'd=saturated
s-=secondary
t- or tert-=tertiary
TBDMS=t-butyldimethylsilyl
TFA=trifluoroacetic acid
THF=tetrahydrofuran
TMS=trimethylsilyl
tosyl=p-toluenesulfonyl

PHARMACOLOGICAL AND BEHAVIORAL ASSAYS

Receptor-Binding Assays: Competition-binding assays in MOR-CHO (mu), DOR-CHO (delta) and KOR-CHO (kappa) were performed at 25° C. in 50 mM potassium phosphate buffer, pH 7.4, containing 5 mM magnesium sulfate (only in the case of CHO-MOR). Specific binding was defined as the difference between total binding and nonspecific binding, determined in the presence of 8 µM levallorphan. 125I-SMGP1 (IBNtxA) was used as the universal radioligand to determine the relative affinity of drugs in MOR1-CHO, KOR1-CHO and DOR1-CHO. Protein concentrations were generally 20-40 µg/mL, incubation times were 150 minutes for all assays. (Majumdar et al., Bioorg Med Chem Lett. 2011, 21(13), 4001-4004). Kappa3 opioid receptor competition binding assays were carried out in whole brain membrane homogenates, performed at 25° C. in 50 mM potassium phosphate buffer, pH 7.4, containing 5 mM magnesium sulfate for 90 minutes in presence of 100 nM CTAP, 100 nM U50488h and 100 nM DPDPE. $^{125}$I-SMGP1 was used as the radioligand in the assays, typically 500 micrograms of protein and 0.15 nM of the radioligand was used in a 0.5 mL assay. Specific binding was defined as the difference between total binding and nonspecific binding, determined in the presence of 1 µM levallorphan. Protein concentration was determined as described by Lowry et al. [J Biol Chem 1951, 193, 265-275; (1951)] using bovine serum albumin as the standard. Kd, Bmax, and Ki values were calculated by nonlinear regression analysis (GraphPadPrism). We have observed that compounds that bind with the kappa3 site and that exhibit $K_i$ less than 100 nM exhibit useful analgesia, and compounds that are selective for kappa3 exhibit improved side-effect profiles. The "kappa3 opioid receptor" as referred to herein is the receptor first characterized by Clark et al. [*J. Pharmacol. Exp. Ther.* 21, 461-468 (1989)]. This receptor appears to be the same receptor which has been alternately referred to as the kappa2b receptor by Rothman et al. [*Peptides* 11, 311-331 (1990)]. In any event, it can be characterized by the high affinity binding ($K_i$<1 nM) for levallorphan, ketocyclazocine and SMGP1 and low affinity for morphine ($K_i$>1 µM), norbinaltorphimine ($K_i$>50 nM) and DADL ($K_i$>50 nM).

Tail Flick Analgesia Assays: Male CD-i mice (25-35 g; Charles River Breeding Laboratories, Wilmington, Mass.) were maintained on a 12-hr light/dark cycle with Purina rodent chow and water available ad libitum. Mice were housed in groups of five until testing. Analgesia was determined using the radiant heat tail-flick technique [D'Amour and Smith, *J. Pharmacol. Exp. Ther.* 72: 74-79 (1941)]. For the tail-flick assay, the latency to withdraw the tail from a focused light stimulus was measured electronically using a photocell. Baseline latencies (2.0-3.0 sec) were determined before experimental treatments for all animals as the mean of two trials. Post-treatment tail-flick latencies were determined as indicated for each experiment, and a maximal latency of 10 sec for tail-flick was used to minimize tissue damage. All experiments were replicated at least twice with each group in each experiment containing at least 10 mice and the combined results of all replications presented. Compounds with an $ED_{50}$ less than 10 mg/kg are preferred because the potency allows for smaller dosages, but higher $ED_{50}$'s are possible.

Gastrointestinal motility assay: Gastrointestinal transit was determined as described by Paul and Pasternak [*Eur. J. Pharmacol.* 149 (1988), pp. 403-404)]. In brief, after withholding food for 8 hours, animals received the indicated drug and then were given a charcoal meal (0.2 mL; 10% of purified charcoal and 2.5% of gum tragacanth, w/v) by gavage and were sacrificed 30 min later. The distance traveled by the charcoal meal was then measured and reported in centimeters.

Conditional place preference/Aversion and Locomotor activity: The testing apparatus consisted of two compartments of equal size separated by a wall with a guillotine-style door (MedAssociates ENV-512 insert). One compartment was surrounded by white walls and had a rod floor, while the other had black walls and a grid floor. Infrared photobeams lining the floor of the compartments were used to track the location of the mouse at all times; this data was used to calculate the total distance traveled by the animal using MedAssociates Activity Monitor software. This data is expressed as the distance each animal traveled following each drug injection divided by the average distance traveled by that animal following saline injection.

For 2 days prior to testing, the animal cages were brought to the testing room for 3 hours for habituation to the environment. On the pre-conditioning test day, animals are placed in one chamber and allowed to explore both sides freely for 20 minutes. Their baseline preferences for each compartment are calculated; in the place preference experiment, the side in which they spend more time in initially is assigned to saline, while the opposite side is designated as the drug-paired side. For place aversion, the initially preferred side is paired with drug, while the other side is assigned to saline. During the conditioning phase of the experiment, animals are allowed to habituate to the experimental room for 1 hour prior to each session. Animals are injected on alternating days for 8 days with either drug or saline and restricted to one compartment for 20 minutes so that they learn to associate a treatment condition with a specific compartment. On the post-conditioning testing day, animals are placed in the side paired with saline and allowed to freely explore both compartments for 20 minutes. The time spent in each compartment post-conditioning is calculated and subtracted from the amount of time spent in each compartment pre-conditioning to determine the change in each animals' preference due to conditioning.

Determination of $LD_{50}$: Lethality was determined 60 minutes after the administration of test compound (250 mg/kg) to groups of mice (n=8). See Gistrak et al. *The Journal of Pharmacology and Experimental Therapeutics*. 251, 469-476 (1989).

Tolerance studies: Groups of mice (n=10) were treated with either morphine (6 mg/kg s.c.) or test compound (1 mg/kg s.c.) twice daily for 5 days. Tail-flick lateneies were determined before and 30 minutes after each injection. Scc Gistrak et al. (1989) op. cit. Effects of Chronic administration: Mice were pelleted with morphine pellets (75 mg free base; NIDA) and tested for analgesia on Day 1 and 3. On Day 3 they also were tested with test compound (1 mg/kg, s.c.) for analgesia and with naloxone (1 mg/kg, s.c.) to precipitate withdrawal. A separate group of mice received test compound alone as a control for its analgesia in the morphine-tolerant mice. Similarly, a group of mice (n=10) were made tolerant to test compound by twice daily injections to 1 mg/kg, s.c. for 10 days. On Day 10 they also were tested with test compound (1 mg/kg, s.c.) for analgesia and with naloxone (1 mg/kg, s.c.) and levallorphan (1 mg/kg) to precipitate withdrawal. Animals were evaluated for signs of diarrhea and jumping. See Gistrak et al. (1989) op. cit.

Respiratory Depression assessment: The MouseOx Pulse Oximeter system (Starr Life Sciences, Pittsburgh, Pa.) was used to assess respiratory rate in awake, freely-moving, adult male CD1 mice. For 30 minutes, each animal was habituated to the device using a blank collar, after which the oximeter collar was placed on the animal. A five-second average breath rate was assessed at 5 minute intervals. A baseline for each animal was obtained over a 25 minute period prior to drug injection; beginning 15 minutes post-injection, measurements were then taken for a period of 35 minutes. Groups of mice (n=5) were treated subcutaneously with either morphine or test compound and breath rates were measured for both sets. At doses that are five times the $ED_{50}$ of each compound, i.e. 2.5 mg/kg for SMGP1 and 20 mg/kg for morphine, morphine showed 50% respiratory depression whereas SMGP1 showed no statistically significant depression as compared to saline.

Representative results of these studies are outlined in Table 1.

TABLE 1

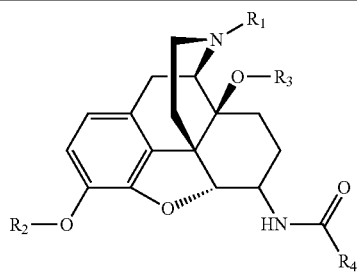

| Compd | $R_1$ | $R_2$ | $R_3$ | $R_4{}^a$ | MOR | KOR | DOR | kappa$_3$ | Tail flick analgesia $ED_{50}$ (mg/kg) |
|---|---|---|---|---|---|---|---|---|---|
| | | | | | \multicolumn{4}{c}{$K_i$ (nM)} | |
| SMGP1 | —CH$_2$cPropyl | H | H | Ph-3I | 0.11 | 0.03 | 0.24 | 0.16 | 0.53 |
| SMGP 2 | —CH$_3$ | H | H | Ph-3I | 0.97 | 47.22 | 2.45 | 41.22 | >10 |

TABLE 1-continued

| Compd | R$_1$ | R$_2$ | R$_3$ | R$_4{}^a$ | K$_i$ (nM) MOR | KOR | DOR | kappa$_3$ | Tail flick analgesia ED$_{50}$ (mg/kg) |
|---|---|---|---|---|---|---|---|---|---|
| SMGP 3 | —CH$_2$CH=CH$_2$ | H | H | Ph-3I | 0.22 | 0.08 | 2.55 | 0.25 | 0.57 |
| SMGP 4 | —CH$_2$CH=CH$_2$ | H | H | Ph-3I$^b$ | 5.07 | 12.16 | 7.642 | 8.46 | 5.0 |
| SMGP 5 | —CH$_2$CH$_2$CH$_3$ | H | H | Ph-3I | | | | 60 | |
| SMGP 6 | —CH$_2$cButyl | H | H | Ph-3I | 0.88 | 0.67 | 2.38 | 11.44 | |
| SMGP 7 | —Bz | H | H | Ph-3I | | | | | |
| SMGP 8 | —CH$_2$CH=CH$_2$ | CH$_3$ | H | Ph-3I | >100 | >100 | >100 | >100 | >10 |
| SMGP 9 | —CH$_2$C$_3$H$_5$ | CH$_3$ | H | Ph-3I | | | | | |
| SMGP 10 | —CH$_3$ | CH$_3$ | H | Ph-3I | | | | | |
| SMGP 11 | —CH$_2$CH=CH$_2$ | COCH$_3$ | H | Ph-3I | | | | | |
| SMGP 12 | —CH$_2$CH=CH$_2$ | CH$_2$OCCH$_3$ | H | Ph-3I | | | | | |
| SMGP 13 | —CH$_2$CH=CH$_2$ | CH$_2$OCCH$_3$ | H | Ph-3I | | | | | |
| SMGP 14 | —CH$_2$CH=CH$_2$ | CH$_2$OCOC(CH$_3$)$_3$ | H | Ph-3I | | | | | |
| SMGP 15 | —CH$_2$CH=CH$_2$ | H | CH$_3$ | Ph-3I | | | | | |
| SMGP 16 | —CH$_2$CH=CH$_2$ | H | H | Ph-2I | 1.56 | 1 | 22.8 | 29 | >10 |
| SMGP 17 | —CH$_2$CH=CH$_2$ | H | H | Ph-4I | 0.11 | 0.28 | 3.36 | 0.64 | 0.16 |
| SMGP 18 | —CH$_2$CH=CH$_2$ | H | H | Ph-3F | 0.47 | 2.05 | 18.19 | 8.09 | 3.24 |
| SMGP 19 | —CH$_2$CH=CH$_2$ | H | H | Ph-3Cl | 1.15 | 0.52 | 4.87 | 5.49 | 2.3 |
| SMGP 20 | —CH$_2$CH=CH$_2$ | H | H | Ph—3Br | 3.85 | 1.58 | 23.37 | 2.05 | 1.36 |
| SMGP 21 | —CH$_2$CH=CH$_2$ | H | H | Ph—H | 4.03 | 14.27 | 60.78 | 5.82 | 5 |
| SMGP 22 | —CH$_2$CH=CH$_2$ | H | H | Ph—3CH$_3$ | 0.29 | 1.62 | 8.24 | 8.98 | 2 |
| SMGP 23 | —CH$_2$CH=CH$_2$ | H | H | Ph—3CF$_3$ | 0.85 | 0.22 | 2.96 | 9.32 | 0.26 |
| SMGP 24 | —CH$_2$CH=CH$_2$ | H | H | Ph—3OCH$_3$ | 0.18 | 4.97 | 17.22 | 1.64 | 0.1 |
| SMGP 25 | —CH$_2$CH=CH$_2$ | H | H | Ph—3NH$_2$ | 0.43 | 0.4 | 36 | 7.62 | >10 |
| SMGP 26 | —CH$_2$CH=CH$_2$ | H | H | Ph—3N(CH$_3$)$_2$ | 6.39 | 34.9 | 51.35 | 10.79 | >10 |
| SMGP 27 | —CH$_2$CH=CH$_2$ | H | H | Ph—3OH | 0.23 | 2.75 | 11.25 | 5.21 | 10.3 |
| SMGP 28 | —CH$_2$CH=CH$_2$ | H | H | Ph—3NO$_2$ | 1.41 | 1.51 | 18.13 | 4.53 | 6.79 |
| SMGP 29 | —CH$_2$CH=CH$_2$ | H | H | Ph—4OCF$_3$ | 0.66 | 3.16 | 17.88 | 7.43 | 0.82 |
| SMGP 30 | —CH$_2$CH=CH$_2$ | H | H | Ph—4OC$_4$H$_9$ | | | | | >10 |
| SMGP 31 | —CH$_2$CH=CH$_2$ | H | H | Ph-4Boronic acid pinacol ester | | | | | >10 |
| SMGP 32 | —CH$_2$CH=CH$_2$ | H | H | Ph—4CH$_2$-tbutyl | | | | | |
| SMGP 33 | —CH$_2$CH=CH$_2$ | H | H | Ph—4Si(OC$_2$H$_5$)$_3$ | | | | | |
| SMGP 34 | —CH$_2$CH=CH$_2$ | H | H | Ph-3,4-I,I | 0.5 | 0.05 | 0.12 | 0.004 | 0.05 |
| SMGP 35 | —CH$_2$CH=CH$_2$ | H | H | Ph-3,4,5-I,I,I | | | | | |
| SMGP 36 | —CH$_2$CH=CH$_2$ | H | H | Ph-3,4-O$_2$C$_2$H$_4$ | | | | | >10 |
| SMGP 37 | —CH$_2$CH=CH$_2$ | H | H | Ph-3,4-O$_2$CH$_2$ | | | | | >10 |
| SMGP 38 | —CH$_2$CH=CH$_2$ | H | H | Ph-3,4-(OC$_2$H$_5$)$_2$ | | | | | |
| SMGP 39 | —CH$_2$CH=CH$_2$ | H | H | Ph-3,4-(OC$_2$H$_4$CF$_3$)$_2$ | | | | | |
| SMGP 40 | —CH$_2$CH=CH$_2$ | H | H | Ph—Ph | 0.95 | 25.79 | 19.15 | 7.17 | 12.5 |
| SMGP 41 | —CH$_2$CH=CH$_2$ | H | H | C$_{14}$H$_{10}$ | 0.74 | 1.29 | 5.51 | 6.64 | 1.47 |
| SMGP 42 | —CH$_2$CH=CH$_2$ | H | H | Ph-cHexane | 1.55 | 49.78 | 45.05 | 7.22 | >10 |
| SMGP43 | —CH$_2$CH=CH$_2$ | H | H | PhCH$_2$Ph | | | | | |
| SMGP 44 | —CH$_2$CH=CH$_2$ | H | H | PhOPh | | | | | |
| SMGP 45 | —CH$_2$CH=CH$_2$ | H | H | Anthracene | | | | | |
| SMGP 46 | —CH$_2$CH=CH$_2$ | H | H | Ph—Ph—Ph | | | | | |
| SMGP 47 | —CH$_2$CH=CH$_2$ | H | H | 2-Quinoline | 0.2 | 0.5 | 150 | 0.01 | 0.04 |
| SMGP 48 | —CH$_2$CH=CH$_2$ | H | H | Ph-4Benzofuran | | | | | |
| SMGP 49 | —CH$_2$CH=CH$_2$ | H | H | Ph-4Thiophene | | | | | |
| SMGP 50 | —CH$_2$CH=CH$_2$ | H | H | Ph-4Benzopyrrole | | | | | |
| SMGP51 | —CH$_2$CH=CH$_2$ | H | H | Ph-4(2-Furan) | | | | | >10 |
| SMGP52 | —CH$_2$CH=CH$_2$ | H | H | Ph-4(2-Thiophene) | | | | | |
| SMGP 53 | —CH$_2$CH=CH$_2$ | H | H | Ph-4(2-Pyrrole) | | | | | |
| SMGP 54 | —CH$_2$CH=CH$_2$ | H | H | CH$_3$ | 20.46 | >100 | >100 | >100 | >10 |
| SMGP 55 | —CH$_2$CH=CH$_2$ | H | H | C$_6$H$_{13}$ | 9.5 | 9.15 | 32.2 | 29.65 | >10 |
| SMGP 56 | —CH$_2$CH=CH$_2$ | H | H | C$_{12}$H$_{25}$ | 0.61 | 9.35 | 32.2 | 29.65 | >10 |
| SMGP 57 | —CH$_2$CH=CH$_2$ | H | H | cHexane | 11.54 | 17.9 | >100 | 30.17 | >10 |

TABLE 1-continued

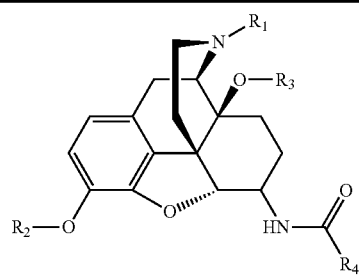

| Compd | $R_1$ | $R_2$ | $R_3$ | $R_4{}^a$ | MOR | KOR | DOR | kappa$_3$ | Tail flick analgesia $ED_{50}$ (mg/kg) |
|---|---|---|---|---|---|---|---|---|---|
| SMGP 58 | —CH$_2$CH=CH$_2$ | H | H | Adamantane | 6.5 | 7.1 | >100 | 30.27 | >10 |
| SMGP59 | —CH$_2$CH=CH$_2$ | H | H | Ph—4-SCH$_3$ | 0.8 | 3.67 | 15.87 | 4.08 | 5.43 |

$^a$Beta isomer
$^b$Alpha isomer

Compound SMGP1, which had both high affinity and high selectivity for kappa3 receptors, was examined more extensively. Compound SMGP1 is a very potent analgesic in mice, having a potency greater than morphine. However, the pharmacology of the drug differed from morphine in a number of important criteria. Naloxone is an effective antagonist, capable of reversing morphine and virtually all the clinically used opiates. However, naloxone was far less potent in reversing the analgesia elicited by SMGP1, and a series of antagonists selective against traditional mu, delta, kappa1 and ORL1 drugs were inactive. Levallorphan is an opioid antagonist structurally analogous to the opioid agonist levorphanol. Like levorphanol, levallorphan has high affinity for the kappa3 site. Thus, it was not surprising that levallorphan effectively reversed the analgesic actions of compound 1. This confirms the opioid nature of the response. Chronic administration of morphine rapidly leads to a diminished response, or tolerance.

Compound SMGP1 also showed some tolerance with chronic administration, although it appeared more slowly than that seen with morphine. However, SMGP1 showed no cross tolerance to morphine. When given to highly morphine tolerant mice, SMGP1 showed a normal analgesic response. Following chronic administration, all animals administered morphine show prompt and dramatic signs of withdrawal, a measure of physical dependence, when challenged with an antagonist. In contrast, chronic administration of SMGP1 led to no physical dependence. Naloxone did not precipitate withdrawal, which was expected since it also did not reverse the analgesia at this dose and had poor affinity for the binding site. However, levallorphan also did not precipitate withdrawal despite its ability to reverse analgesia, clearly distinguishing SMGP1 from clinically available opioids. Unlike other kappa drugs currently available clinically, SMGP1 could be used in conjunction with traditional opiates regardless of how long a patient had been taking them, i.e. they could be used to reduce pain in a μ-opioid-dependent patient. The effect of SMGP1 on the inhibition of gastrointestinal transit was minimal. This is in marked contrast to morphine. Based upon these observations, a person of skill would conclude that SMGP1 would have minimal constipation liability.

Compounds of the invention may be synthesized via the following general route:

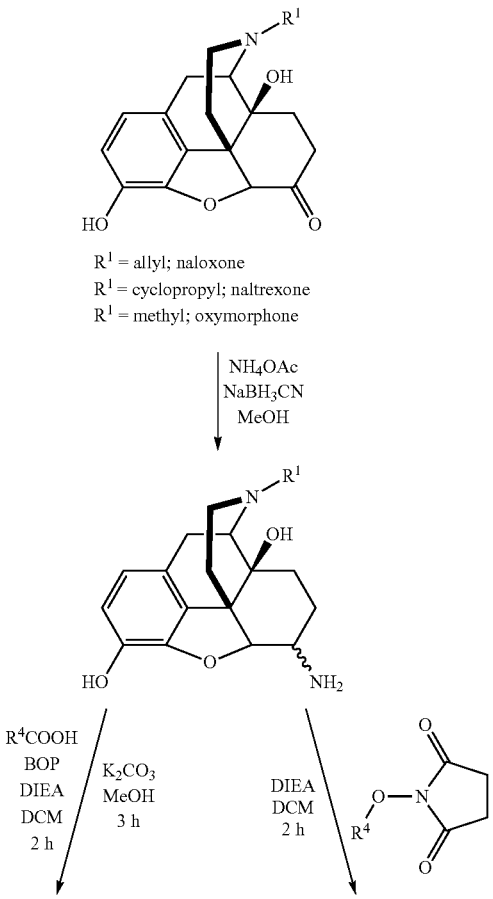

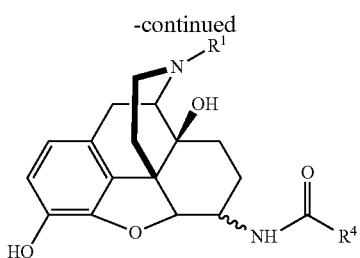

This synthesis may be extended for compounds in which $R^2$ is other than hydrogen:

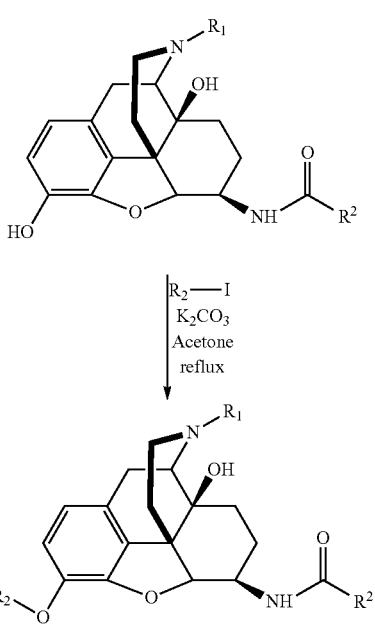

$R^2 = $ —COCH$_3$ or —CH$_2$OCOCH$_3$ or —CH$_2$OCO$_2$CH$_3$ or —CH$_2$OCO(CH$_3$)$_3$

Detailed descriptions of the synthesis of representative compounds of the invention follow:

General Procedures: All reactions were carried out under positive nitrogen atmosphere with a magnetic stirrer at ambient temperatures using oven dried glassware. $^1$H-NMR were taken on a 500 MHz Bruker instrument using CDCl$_3$ as solvent. Silica gel (230-400 mesh) was used in column chromatography.

The ketone at the 6-position of the three opiates was transformed to an amine (Opiate-NH$_2$) by reductive amination using NaBH$_3$CN and NH$_4$OAc to yield a mixture of beta and alpha isomers. The beta and alpha isomers were purified by column chromatography. In a parallel synthesis, substituted carboxylic acids were converted to N-succinimidyl ester by reacting it with N-hydroxysuccinimide in presence of DCC and THF. The corresponding activated ester was then reacted with the beta or alpha isomer of the Opiate-NH$_2$ in presence of DIEA and DCM. The aroyl amido derivatives of opiates were then purified by column chromatography. Alternatively, the substituted carboxylic acids were directly coupled to the Opiate-NH$_2$ using BOP and DIEA in DCM to give 3,6-diaroylated derivatives. The 3,6-diaroyl opiate derivatives were then subjected to basic hydrolysis with K$_2$CO$_3$ to yield 6-aroyl derivatives of naltrexamine, naloxamine and oxymorphanamine.

Reductive amination of naltrexone, naloxone and oxymorphone was carried out using a literature protocol published by Portoghese and co-workers (*J Med Chem* 1977 (20), 8, 1100). Typically, 10 g of opiate (30 mmol), was stirred with NH$_4$OAc (22 g, 0.3 mol, 10 eqv) in 40 mL dry methanol for 10 minutes at room temperature. NaBH$_3$CN (1.31 g, 21 mmol, 0.7 eqv) in 5 mL dry methanol was then added to the reaction mixture and contents stirred overnight. The reaction was quenched by addition of 10 mL 1N NaOH, the solvents were evaporated on a rotavapor at 40° C. The residue was then extracted with 30 mL DCM three times; the organic extracts were combined and washed with 25 mL water. The organic extracts were dried over Na$_2$SO$_4$ and concentrated to a white solid, which was purified by silica gel column chromatography. The reaction gave a mixture of alpha and beta isomers. The respective isomers were isolated by column chromatography using 87:10:3 of EtOAc:MeOH:NH$_4$OH as the eluent. The beta isomer had a higher $R_f$ than the alpha isomer on a TLC plate and eluted first when the mixture was subjected to column chromatography. Yields for beta isomer were about 2.5-3 g (25-30%). NMR peaks of the compounds matched the literature values.

N-hydroxysuccinimide (NHS) esters of substituted carboxylic acids were synthesized as follows: Substituted carboxylic acid (7.8 mmol), NHS (1 g, 8.6 mmol, 1.1 eqv), DCC (1.79 g, 8.6 mmol, 1.1 eqv) in 20 mL dry THF were stirred overnight. The white suspension was filtered and the clear filterate was evaporated on a rotavapor at 40° C. The white solid seen was purified by column chromatography using EtOAc/hexanes as eluents. A singlet at $\delta 2.9$ integrating to 4 protons in $^1$H-NMR and corresponding to four protons of succinimide was seen in all NHS esters of substituted carboxylic acids. Yields were about 80-100%.

Aroylations of naltrexamine, naloxamine and oxymorphonamine were carried out as follows: Procedure I: Opiate-NH$_2$ (200 mg, 0.6 mmol) was reacted with DIEA (116 ul, 0.66 mmol, 1.1 eqv) and NHS esters of substituted carboxylic acids (0.66 mmol, 1.1 eqv) in dry DCM (5 mL) for 2 h. The reaction was diluted to 20 mL with DCM and washed with 5 mL water. The organic extracts were dried over Na$_2$SO$_4$ and then concentrated to a white solid, which was purified by silica gel column chromatography using 1-5% MeOH:DCM as eluents. Yields of the target compounds were 50-75%.

Alternate procedure II: Opiate-NH$_2$ (200 mg, 0.6 mmol) was reacted with BOP (271 mg, 1.2 mmol, 2 eqv), DIEA (313 ul, 1.8 mmol, 3 eqv) and substituted carboxylic acid (1.2 mmol, 2 eqv) in dry DCM (5 mL) for 2 h. The reaction mixture poured into a small silica gel column and eluted with 100 mL EtOAc. The ethyl acetate fraction was evaporated and a white solid was obtained. The solid obtained was hydrolyzed in K$_2$CO$_3$ and MeOH. Briefly, the contents, usually a white suspension were stirred with K$_2$CO$_3$ (622 mg, 4.22 mmol, 7 eqv) and McOH for 3 h. The white suspension seen was filtered and the filterate concentrated to a yellowish oil or a white solid. The oily residue or white solid obtained was then purified by column chromatography using 1-5% MeOH:DCM as the eluent. Typical yields were around 65%.

Synthesis of Individual Embodiments:

SMGP1: Compound SMGP1 was synthesized according to the general procedure (1) described above using β-naltrexamine, NHS ester of 3-iodobenzoic acid and DIEA in DCM. A white solid was obtained. $^1$H-NMR δ: 8.16 (s, 1H), 7.8-7.74 (m, 2H), 7.35-7.34 (d, 1H), 7.14-7.11 (m, 1H), 6.68-6.67 (d, 1H), 6.56-6.54 (d, 1H), 4.59 (d, 1H), 4.12 (m, 1H), 3.15-3.0 (m, 2H), 2.67-2.61 (m, 2H), 2.39-2.36 (m, 2H), 2.26-2.19 (m, 2H), 1.19 (m, 1H), 1.59-1.47 (m, 4H), 0.84 (m, 1H), 0.5 (m, 2H), 0.13 (m, 2H). ESI-MS m/z: 573.2 (MH$^+$).

SMGP2: Compound SMGP2 was synthesized according to the general procedure (I) described above using β-oxymorphanamine, NHS ester of 3-iodobenzoic acid and DIEA in DCM. A white solid was obtained. $^1$H-NMR δ: 8.13 (s, 1H), 7.8-7.78 (d, 2H), 7.76-7.76 (d, 1H), 7.14-7.11 (m, 1H), 6.73-6.71 (d, 1H), 6.57-6.59 (d, 1H), 4.55 (d, 1H), 4.12 (m, 1H), 3.16-3.12 (m, 1H), 2.88 (m, 1H), 2.65-2.62 (m, 1H), 2.47 (m, 1H), 2.36 (s, 3H), 2.25-2.22 (m, 2H), 1.9-1.25 (m, 5H). ESI-MS m/z: 533.13 (MH$^+$).

SMGP3: SMGP 3 was synthesized according to the general procedure (I) described above using β-naloxamine, NHS ester of 3-iodobenzoic acid and DIEA in DCM. A white solid was obtained. Yield: 75%; $^1$H-NMR (500 MHz, CDCl$_3$) δ: 8.16 (s, 1H), 7.8 (d, J=8.9 Hz, 1H), 7.76 (d, J=8.9 Hz, 1H), 7.15-7.11 (m, 1H), 6.69 (d, J=10.6 Hz, 1H), 6.57 (d, J=10.6 Hz, 1H), 5.8 (m, 1H), 5.23-5.16 (m, 2H), 4.57 (d, J=8.85 Hz, 1H), 4.13 (m, 1H), 3.14-1.2, 14H). $^{13}$C NMR (600 MHz, CDCl$_3$) δ: 165.4, 142.9, 140.3, 139.2, 136.4, 136.2, 135.2, 130.6, 130.1, 126.1, 124.7, 119.3, 118.1, 117.6, 94.3, 92.9, 70.2, 62.4, 57.8, 50.5, 47.3, 43.6, 31.5, 29.0, 23.2, 22.7 ppm. ESI-MS m/z: 559.1 (MH$^+$). HRMS calcd for C$_{26}$H$_{28}$N$_2$O$_4$I (MH+), 559.1094; found, 559.1099.

SMGP4: SMGP4 was synthesized according to the general procedure (I) described above using α-naloxamine, NHS ester of 3-iodobenzoic acid and DIEA in DCM. A white solid was obtained. Yield: 73%; $^1$H-NMR (500 MHz, CDCl$_3$) δ: 8.01 (s, 1H), 7.78 (d, J=7.8 Hz, 1H), 7.66 (d, J=7.8 Hz, 1H), 7.11 (t, J=7.8 Hz, 1H), 6.70 (d, J=8.1 Hz, 1H), 6.56 (d, J=8.1 Hz, 1H), 6.37 (d, J=8.2 Hz, 1H), 5.80 (m, 1H), 5.18 (d, J=18.5 Hz, 1H), 5.15 (d, J=10.9 Hz, 1H), 4.74 (m, 2H), 3.50-1.00 (m, 15H) ppm. $^{13}$C NMR (600 MHz, CDCl$_3$) δ: 165.5, 145.1, 140.3, 137.2, 136.6, 136.0, 135.2, 130.8, 130.1, 126.3, 125.9, 119.4, 118.0, 117.3, 94.2, 90.1, 69.7, 62.3, 58.1, 47.2, 46.7, 42.9, 33.3, 28.9, 23.0, 21.0 ppm. MS (ESI) m/z (%) 559 (MH+). HRMS calcd for C$_{26}$H$_{28}$N$_2$O$_4$I (MH+), 559.1094; found, 559.1107.

SMGP8: SMGP8 was synthesized according to the general procedure (I) described above using 3-OMe-β-naloxamine, NHS ester of 3-iodobenzoic acid and DIEA in DCM. A white solid was obtained. Yield: 36%; $^1$H-NMR δ: 8.19 (s, 1H), 7.8 (m, 1H), 7.42 (m, 1H), 7.16 (m, 1H), 6.75 (d, J=10 Hz, 1H), 6.66 (d, J=10 Hz, 1H), 5.85 (m, 1H), 5.18 (m, 2H), 4.61 (d, 1H), 4.08 (m, 1H), 3.85 (s, 2H), 3.15-0.1 (m, 14H). MS (ESI) m/z (%) 573 (MH+). HRMS calcd for C$_{27}$H$_{30}$N$_2$O$_4$I (MH+), 573.1250; found, 573.1252.

SMGP16: SMGP16 was synthesized according to the general procedure (II) described above using β-naloxamine, 2-iodobenzoic acid, BOP and DIEA in DCM followed by base hydrolysis. A white solid was obtained. Yield: 60%; $^1$H-NMR (500 MHz, CDCl$_3$) δ: 7.87 (d, J=8.35 Hz, 1H), 7.42 (d, J=8.35 Hz, 1H), 7.38-7.36 (m, 1H), 7.11-7.08 (m, 1H), 6.75 (d, J=8.35 Hz, 1H), 6.6 (d, J=8.35 Hz, 1H), 6.41 (m, 1H), 5.78 (m, 1H), 5.14 (m, 2H), 4.51 (d, J=8.35 Hz, 1H), 4.17 (m, 1H), 3.49-1.26 (m, 14H). $^{13}$C NMR (600 MHz, CDCl$_3$) δ: 169.2, 142.9, 142.2, 139.9, 139.6, 135.2, 131.1, 130.8, 128.3, 128.2, 124.8, 119.3, 118.0, 117.6, 93.2, 92.4, 70.2, 62.4, 57.7, 50.8, 47.5, 43.6, 31.0, 29.5, 23.5, 22.7 ppm. MS(ESI) m/z (%) 559 (MH+). HRMS calcd for C$_{26}$H$_{28}$N$_2$O$_4$I (MH+), 559.1094; found, 559.1115.

SMGP17: SMGP17 was synthesized according to the general procedure (II) described above using β-naloxamine, 4-iodobenzoic acid, BOP and DIEA in DCM followed by base hydrolysis. A white solid was obtained. Yield: 43%; $^1$H-NMR (500 MHz, CDCl$_3$) δ: 7.78 (d, J=9.8 Hz, 2H), 7.53 (d, J=9.8 Hz, 2H), 6.7 (d, J=9.8 Hz, 1H), 6.57 (d, J=9.8 Hz, 1H), 5.82 (m, 1H), 5.23-5.2 (m, 2H), 4.51 (d, J=8.2 Hz, 1H), 4.23 (m, 1H), 3.19-1.5 (m, 14H). $^{13}$C NMR (600 MHz, Methanol-d4) δ 169.3, 143.8, 143.1, 139.0, 138.9, 135.1, 130.3, 130.0, 99.4, 91.9, 71.4, 64.7, 56.7, 53.3, 49.6, 47.7, 45.8, 31.1, 28.9, 24.6, 24.0 ppm. MS(ESI) m/z (%) 559 (MH+). HRMS calcd for C$_{26}$H$_{28}$N$_2$O$_4$I (MH+), 559.1094; found, 559.1099.

SMGP18: SMGP18 was synthesized according to the general procedure (II) described above using β-naloxamine, 3-fluorobenzoic acid, BOP and DIEA in DCM followed by base hydrolysis. A white solid was obtained. Yield: 70%, $^1$H-NMR (500 MHz, CDCl$_3$) δ: 7.59 (d, J=9.2 Hz, 1H), 7.55 (d, J=9.2 Hz, 1H), 7.41-7.36 (m, 2H), 7.21-7.17 (m, 1H), 6.73 (d, J=9.2 Hz, 1H), 6.59 (d, J=10 Hz, 1H), 5.81 (m, 1H), 5.23-5.16 (m, 2H), 4.51 (d, J=9.2 Hz, 1H), 4.25 (m, 1H), 3.14-1.28 (m, 14H). MS(ESI) m/z (%) 451 (MH+). HRMS calcd for C$_{26}$H$_{28}$N$_2$O$_4$F (MH+), 451.2033; found, 451.2031.

SMGP19: SMGP19 was synthesized according to the general procedure (II) described above using β-naloxamine, 3-chlorobenzoic acid, BOP and DIEA in DCM followed by base hydrolysis. A white solid was obtained. Yield: 72%, $^1$H-NMR (500 MHz, CDCl$_3$) δ: 7.82 (s, 1H), 7.69 (d, J=7.85 Hz, 1H), 7.47 (d, J=7.85 Hz, 1H), 7.39-7.35 (m, 1H), 6.73 (d, J=8.05 Hz, 1H), 6.59 (d, J=8.05 Hz, 1H), 5.82-5.81 (m, 1H), 5.2-5.17 (m, 2H), 4.51-4.5 (d, J=5 Hz, 1H), 4.25 (m, 1H), 3.14-1.28 (m, 14H). $^{13}$C NMR (600 MHz, CDCl$_3$) δ 165.7, 142.9, 139.2, 136.1, 135.2, 134.6, 131.5, 130.5, 129.8, 127.5, 125.1, 124.7, 119.3, 118.1, 117.6, 92.7, 70.3, 62.4, 57.8, 50.5, 47.2, 43.6, 31.6, 29.0, 23.2, 22.7 ppm. MS(ESI) m/z (%) 467 (MH+). HRMS calcd for C$_{26}$H$_{28}$N$_2$O$_4$Cl (MH+), 467.1738; found, 467.1737.

SMGP20: SMGP20 was synthesized according to the general procedure (II) described above using β-naloxamine, 3-bromobenzoic acid, BOP and DIEA in DCM followed by base hydrolysis. A white solid was obtained. Yield: 70%; $^1$H-NMR (500 MHz, CDCl$_3$) δ: 7.96 (s, 1H), 7.72 (d, J=8.75 Hz, 1H), 7.61 (d, J=8.75 Hz, 1H), 7.31-7.28 (m, 1H), 7.24-7.22 (m, 1H), 6.72 (d, J=8.75 Hz, 1H), 6.58 (d, J=8.75 Hz, 1H), 5.8 (m, 1H), 5.23-5.16 (m, 2H), 4.52 (d, J=8.75 Hz, 1H), 4.18 (m, 1H), 3.14-1.5 (m, 14H). MS (ESI) m/z (%) 511 (MH+). HRMS calcd for C$_{26}$H$_{28}$N$_2$O$_4$Br (MH+), 511.1232; found, 511.1250.

SMGP 21: SMGP 21 was synthesized according to the general procedure (II) described above using β-naloxamine, benzoic acid, BOP and DIEA in DCM followed by base hydrolysis. A white solid was obtained. Yield: 32%; $^1$H-NMR (500 MHz, CDCl$_3$) δ: 7.82 (d, J=9.2 Hz, 2H), 7.51-7.42 (m, 3H), 7.20 (m, 1H), 6.74 (d, J=9.2 Hz, 1H), 6.59 (d, J=9.2 Hz, 1H), 5.82 (m, 1H), 5.23-5.17 (m, 2H), 4.5 (d, J=7.65 Hz, 1H), 4.26 (m, 1H), 3.13-1.25 (m, 14H). $^{13}$C NMR (600 MHz, CDCl$_3$) δ 166.9, 143.3, 139.2, 135.2, 134.5, 131.5, 130.7, 128.6, 127.0, 125.0, 119.2, 118.1, 117.5, 93.3, 70.2, 62.5, 57.8, 49.8, 47.2, 43.6, 31.7, 28.9, 23.2, 22.7 ppm. MS (ESI) m/z (%) 433 (MH+). HRMS calcd for C$_{26}$H$_{29}$N$_2$O$_4$ (MH+), 433.2127; found, 433.2125.

SMGP 22: SMGP 22 was synthesized according to the general procedure (II) described above using β-naloxamine, 3-toluic acid, BOP and DIEA in DCM followed by base hydrolysis. A white solid was obtained. Yield: 49%; $^1$H-NMR (500 MHz, CDCl$_3$) δ: 7.67 (m, 2H), 7.51 (s, 1H), 7.35 (d, J=8.1 Hz, 1H), 6.71 (d, J=8.1 Hz, 1H), 6.61 (d, J=8.1 Hz, 1H), 5.82 (m, 1H), 5.23-5.17 (m, 2H), 4.55 (d, J=7.05 Hz, 1H), 4.06 (m, 1H), 3.36-1.5 (m, 16H). $^{13}$C NMR (600 MHz, CDCl$_3$) δ 167.3, 143.1, 139.3, 138.4, 135.2, 134.4, 132.3, 130.7, 128.4, 127.8, 124.8, 123.9, 119.2, 118.1, 117.6, 93.3, 70.2, 62.5, 57.8, 50.2, 47.3, 43.6, 31.5, 29.1, 23.5, 22.7, 21.4 ppm. MS(ESI) m/z (%) 447 (MH+). HRMS calcd for $C_{27}H_{31}N_2O_4$ (MH+), 447.2284; found, 447.2290.

SMGP 23: SMGP 23 was synthesized according to the general procedure (II) described above using β-naloxamine, 3-trifluorotoluic acid, BOP and DIEA in DCM followed by base hydrolysis. A white solid was obtained. Yield: 69%; $^1$H-NMR (500 MHz, CDCl$_3$) δ: 8.01 (s, 3H), 8.0 (m, 1H), 7.89-7.88 (m, 1H), 7.65 (m, 1H), 7.45 (m, 1H), 6.62 (d, J=8.15 Hz, 1H), 6.5 (d, J=8.15 Hz, 1H), 5.78-5.74 (m, 1H), 5.2-5.13 (m, 2H), 4.67 (d, J=6.15 Hz, 1H), 4.11-4.02 (m, 1H), 3.54-1.24 (m, 14H). $^{13}$C NMR (600 MHz, Methanol-d4) δ 165.7, 142.9, 139.2, 136.1, 135.2, 134.6, 131.5, 130.5, 129.8, 127.5, 125.1, 124.7, 119.3, 118.1, 117.6, 92.7, 70.3, 62.4, 57.8, 50.5, 47.2, 43.6, 31.6, 29.0, 23.2, 22.7 ppm. MS (ESI) m/z (%) 501 (MH+). HRMS calcd for $C_{27}H_{28}N_2O_4F_3$ (MH+), 501.2001; found, 501.2004.

SMGP 24: SMGP 24 was synthesized according to the general procedure (II) described above using β-naloxamine, 3-anisic acid, BOP and DIEA in DCM followed by base hydrolysis. A white solid was obtained. Yield: 60%; $^1$H-NMR (500 MHz, CDCl$_3$) δ: 7.56 (d, J=9 Hz, 1H), 7.39-7.26 (m, 3H), 7.0 (m, 1H), 6.72 (d, J=8.1 Hz, 1H), 6.55 (d, J=8.1 Hz, 1H), 5.78-5.74 (m, 1H), 5.24-5.17 (m, 2H), 4.52 (d, J=6.2 Hz, 1H), 4.12-4.11 (m, 1H), 3.78 (s, 3H), 3.72-1.25 (m, 14H). $^{13}$C NMR (600 MHz, Methanol-d4) δ 170.0, 161.3, 143.8, 143.1, 136.9, 130.7, 127.9, 126.6, 121.8, 121, 120.5, 119.8, 118.6, 113.7, 91.9, 71.4, 64.7, 55.9, 53.2, 49.3, 47.6, 31.1, 29.0, 24.6, 24.1 ppm. MS (ESI) m/z (%) 463 (MH+). HRMS calcd for $C_{27}H_{31}N_2O_5$ (MH+), 463.2233; found, 463.2232.

SMGP 25: SMGP 25 was synthesized according to the general procedure (II) described above using β-naloxamine, 3-amino benzoic acid, BOP and DIEA in DCM followed by base hydrolysis. A white solid was obtained. Yield: 30%; $^1$H-NMR (500 MHz, CDCl$_3$) δ: 7.2-7.16 (m, 1H), 7.1 (d, J=7.95 Hz, 1H), 6.90 (d, J=7.95 Hz, 1H), 6.8 (d, J=7.95 Hz, 1H), 6.75 (d, J=8.1 Hz, 1H), 6.69 (d, J=8.1 Hz, 1H), 5.81-5.8 (m, 1H), 5.19-5.16 (m, 2H), 4.46 (d, J=5.85 Hz, 1H), 4.21-4.19 (m, 1H), 3.48-1.22 (m, 16H). MS (ESI) m/z (%) 448 (MH+). HRMS calcd for $C_{26}H_{30}N_3O_4$ (MH+), 448.2236; found, 448.2230.

SMGP 26: SMGP 26 was synthesized according to the general procedure (II) described above using β-naloxamine, 3-dimethylamino benzoic acid, BOP and DIEA in DCM followed by base hydrolysis. A white solid was obtained. Yield: 60%; $^1$H-NMR (500 MHz, CDCl$_3$) δ 7.63 (s, 1H), 7.53 (d, J=6.0 Hz, 1H), 7.47 (t, J=6.8 Hz, 1H), 7.33 (dd, J=6.8, 1.8 Hz, 1H), 6.77 (s, 1H), 6.76 (s, 1H), 5.93 (m, 1H), 5.68 (d, J=14.5 Hz, 1H), 5.62 (d, J=8.5 Hz, 1H), 4.81 (d, J=6.5 Hz, 1H), 3.95-1.55 (m, 23H) ppm. MS (ESI) m/z (%) 476 (MH+). HRMS calcd for $C_{28}H_{34}N_3O_4$ (MH+), 476.2549; found, 476.2544.

SMGP 27: SMGP 27 was synthesized according to the general procedure (II) described above using β-naloxamine, 3-hydroxy benzoic acid, BOP and DIEA in DCM followed by base hydrolysis. A white solid was obtained. Yield: 39%; $^1$H-NMR (500 MHz, CDCl$_3$) δ: 7.44 (m, 3H), 7.3-7.28 (m, 2H), 6.99 (d, J=7.75 Hz, 1H), 6.71 (d, J=7.75 Hz, 1H), 6.6 (d, J=7.75 Hz, 1H), 5.82-5.8 (m, 1H), 5.22-5.17 (m, 2H), 4.51 (d, J=7.75 Hz, 1H), 4.062 (m, 1H), 3.51-1.51 (m, 14H). MS (ESI) m/z (%) 449 (MH+). HRMS calcd for $C_{26}H_{29}N_2O_5$ (MH+), 449.2076; found, 449.2080.

SMGP 28: SMGP 28 was synthesized according to the general procedure (II) described above using β-naloxamine, 3-nitro benzoic acid, BOP and DIEA in DCM followed by base hydrolysis. A white solid was obtained. Yield: 59%; $^1$H-NMR (500 MHz, CDCl$_3$) δ: 8.68 (s, 1H), 8.36-8.34 (m, 1H), 8.22 (d, J=11.8 Hz, 1H), 7.67-7.63 (m, 2H), 6.69 (d, J=11.8 Hz, 1H), 6.58 (d, J=11.8 Hz, 1H), 5.81 (m, 1H), 5.2-5.17 (m, 2H), 4.59 (d, J=9.8 Hz, 1H), 4.27 (m, 1H), 3.14-1.25 (m, 14H). MS(ESI) m/z (%) 478 (MH+). HRMS calcd for $C_{26}H_{28}N_3O_6$(MH+), 479.1978; found, 478.1967.

SMGP 29: SMGP 29 was synthesized according to the general procedure (II) described above using β-naloxamine, 4-(trifluoromethoxy)benzoic acid, BOP and DIEA in DCM followed by base hydrolysis. A white solid was obtained. Yield: 79%; $^1$H-NMR (500 MHz, CDCl$_3$) δ: 7.87 (d, J=11.75 Hz, 1H), 7.44 (d, J=11.75 Hz, 1H), 7.24 (d, 2H), 6.72 (d, J=11.75 Hz, 1H), 6.58 (d, J=11.75 Hz, 1H), 5.81 (m, 1H), 5.23-5.16 (m, 2H), 4.53 (d, J=9.8 Hz, 1H), 4.24 (m, 1H), 3.33-1.28 (m, 14H). $^{13}$C NMR (600 MHz, Methanol-d4) δ 168.7, 152.8, 143.8, 143.2, 134.5, 130.6, 127.9, 126.6, 122.7, 121.8, 121.0, 119.7, 91.9, 71.4, 64.7, 56.7, 53.3, 48.3, 47.6, 31.1, 28.9, 24.6, 24.1 ppm. MS (ESI) m/z (%) 517 (MH+). HRMS calcd for $C_{27}H_{28}N_2O_5F_3$ (MH+), 517.1950; found, 517.1956.

SMGP30: Compound SMGP30 was synthesized according to the general procedure (II) described above using β-naloxamine, 4-butoxybenzoic acid, BOP and DIEA in DCM followed by base hydrolysis. A white solid was obtained. $^1$H-NMR δ: 7.77-7.75 (d, 2H), 7.22 (d, 1H), 6.88-6.86 (d, 2H), 6.73-6.71 (d, 1H), 6.57-6.55 (d, 1H), 5.79 (m, 1H), 5.22-5.15 (m, 2H), 4.52 (d, 1H), 4.17 (m, 1H), 3.99 (t, 2H), 3.47-0.97 (m, 21H) ESI-MS m/z: 503.24 (MH$^-$).

SMGP34: SMGP34 was synthesized according to the general procedure (II) described above using β-naloxamine, 3,4-diiodobenzoic acid, BOP and DIEA in DCM followed by base hydrolysis. A white solid was obtained. Yield: 63%; $^1$H-NMR δ: 8.29 (s, 1H), 7.91 (d, J=9.1 Hz, 1H), 7.44 (d, J=9.1 Hz 1H), 6.7 (d, J=9.9 Hz, 1H), 6.66 (d, J=9.9 Hz, 1H), 5.85 (m, 1H), 5.18 (m, 2H), 4.61 (d, J=5 Hz, 1H), 4.08 (m, 1H), 3.85 (s, 2H), 3.15-0.1 (m, 14H). $^{13}$C NMR (600 MHz, CDCl$_3$) δ 164.9, 142.1, 139.3, 139.2, 137.9, 135.1, 130.4, 127.5, 124.5, 119.5, 118.2, 117.6, 112.1, 108.2, 92.4, 70.4, 62.4, 57.8, 51.4, 47.3, 43.6, 31.2, 29.5, 23.5, 22.7 ppm. MS(ESI) m/z (%) 685 (MH+). HRMS calcd for $C_{26}H_{27}N_2O_4I_2$ (MH+), 685.0060; found, 685.0052.

SMGP35: Compound SMGP35 was synthesized according to the general procedure (I) described above using β-naloxamine, NHS ester of 3,4,5-triiodobenzoic acid, and DIEA in DCM. A white solid was obtained. $^1$H-NMR δ: 8.57 (s, 2H), 6.88-6.87 (d, 1H), 6.72-6.7 (d, 1H), 5.83-5.76 (m, 1H), 5.22-5.15 (m, 2H), 4.34 (d, 1H), 4.0 (m, 1H), 3.14-1.5 (m, 14H) ESI-MS m/z: 810.92 (MH+).

SMGP36: Compound SMGP36 was synthesized according to the general procedure (I) described above using β-naloxamine, NHS ester of 1,4-benzodioxane-6-carboxylic acid, and DIEA in DCM. A white solid was obtained. $^1$H-NMR δ: 7.36 (s, 1H), 7.31-7.3 (d, 1H), 7.05-7.03 (d, 1H), 6.88-6.87 (d, 1H), 6.73-6.72 (d, 1H), 6.58-6.56 (d, 1H), 5.84-5.76 (m, 1H), 5.22-5.16 (m, 2H), 4.49-4.48 (d, 1H), 4.28-4.27 (m, 4H), 4.1 (m, 1H), 3.49-1.24 (m, 14H) ESI-MS m/z: 491.10 (MH+).

SMGP40: SMGP40 was synthesized according to the general procedure (I) described above using β-naloxamine, NHS ester of biphenyl-4-carboxylic acid, and DIEA in DCM. A white solid was obtained. Yield: 85%; $^1$H-NMR (500 MHz, CDCl$_3$) δ: 7.89 (d, J=8.15 Hz, 2H), 7.66-7.61 (m, 4H), 7.46 (m, 3H), 7.38 (m, 1H), 6.74 (d, J=8.15 Hz, 1H), 6.61 (d, J=8.15 Hz, 1H), 5.82-5.79 (m, 1H), 5.23-5.17 (m, 2H), 4.53-4.52 (d, J=5.15 Hz, 1H), 4.31-4.29 (m, 1H), 3.15-1.25 (m, 14H). $^{13}$C NMR (600 MHz, CDCl$_3$) δ 166.7, 144.2, 143.2, 140.1, 139.2, 135.2, 133.1, 130.6, 128.9, 128.0, 127.6, 127.2, 119.2, 118.1, 117.6, 92.9, 70.2, 62.5, 57.8, 50.1, 47.2, 43.6, 31.7, 31.0, 28.9, 23.2, 22.7 ppm. MS (ESI) m/z: 509.09 (MH+). HRMS calcd for $C_{32}H_{33}N_2O_4$ (MH+), 509.2440; found, 509.2423.

SMGP41: SMGP41 was synthesized according to the general procedure (I) described above using β-naloxamine, NHS ester of naphthalene-2-carboxylic acid, and DIEA in DCM. A white solid was obtained. Yield: 89%; $^1$H-NMR (500 MHz, CDCl$_3$) δ:

δ 8.17 (s, 1H), 7.78-7.70 (m, 4H), 7.47 (t, J=7.5 Hz, 1H), 7.40 (t, J=7.5 Hz, 1H), 6.91 (d, J=8.8 Hz, 1H), 6.73 (d, J=8.1 Hz, 1H), 6.51 (d, J=8.1 Hz, 1H), 5.79 (m, 1H), 5.16 (m, 2H), 4.80 (m, 1H), 4.73 (d, J=4.3 Hz, 1H), 3.10-1.05 (m, 15H) ppm. $^{13}$C NMR (600 MHz, Methanol-d4) δ 170.0, 147.5, 140.4, 136.4, 134.0, 132.3, 130.1, 129.3, 129.1, 129.0, 128.8, 127.9, 125.1, 123.4, 121.0, 119.6, 89.7, 71.4, 71.0, 63.9, 57.0, 47.7, 47.2, 47.0, 31.8, 30.7, 24.6, 20.9 ppm. MS(ESI) m/z (%) 483 (MH+). HRMS calcd for $C_{30}H_{31}N_2O_4$ (MH+), 483.2284; found, 483.2293.

SMGP42: Compound SMGP42 was synthesized according to the general procedure (I) described above using β-naloxamine, NHS ester of 4-cyclohexylbenzoic acid, and DIEA in DCM. A white solid was obtained. $^1$H-NMR δ: 8.11-8.09 (d, 1H), 7.75-7.73 (d, 2H), 7.26 (d, 2H), 6.73-6.71 (d, 1H), 6.57-6.55 (d, 1H), 5.81 (m, 1H), 5.19 (m, 2H), 4.51 (d, 1H), 4.2 (m, 1H), 3.11-1.1 (m, 14H) ESI-MS m/z: 515.35 (MH$^+$).

SMGP54: SMGP54 was synthesized according to the general procedure (II) described above using β-naloxamine, acetic acid, BOP and DIEA in DCM followed by base hydrolysis. A white solid was obtained. Yield: 33%; $^1$H NMR (500 MHz, CDCl$_3$): δ 6.70 (d, J=8.2 Hz, 1H), 6.56 (d, J=8.2 Hz, 1H), 5.96 (d, J=9.2 Hz, 1H), 5.76 (m, 1H), 5.18 (d, J=17.8 Hz, 1H), 5.14 (d, J=10.5 Hz, 1H), 4.33 (d, J=6.5 Hz, 1H), 3.89 (m, 1H), 3.15-0.80 (m, 18H) ppm. MS(ESI) m/z (%) 371 (MH+). HRMS calcd for $C_{21}H_{27}N_2O_4$ (MH+), 371.1971; found, 371.1965.

SMGP55: SMGP55 was synthesized according to the general procedure (II) described above using β-naloxamine, hexanoic acid, BOP and DIEA in DCM followed by base hydrolysis. A white solid was obtained. Yield: 50%; $^1$H NMR (500 MHz, CDCl$_3$): δ 6.71 (d, J=8.2 Hz, 1H), 6.55 (d, J=8.2 Hz, 1H), 6.07 (d, J=9.2 Hz, 1H), 5.77 (m, 1H), 5.18 (d, J=17.4 Hz, 1H), 5.14 (d, J=10.1 Hz, 1H), 4.34 (d, J=6.4 Hz, 1H), 3.91 (m, 1H), 3.15-0.80 (m, 26H) ppm. MS(ESI) m/z (%) 427 (MH+). HRMS calcd for $C_{26}H_{35}N_2O_4$ (MH+), 427.2597; found, 427.2591.

SMGP56: SMGP56 was synthesized according to the general procedure (11) described above using β-naloxamine, dodecanoic acid, BOP and DIEA in DCM followed by base hydrolysis. A white solid was obtained. Yield: 35%; $^1$H NMR (500 MHz, CDCl$_3$): δ 6.71 (d, J=8.2 Hz, 1H), 6.55 (d, J=8.2 Hz, 1H), 6.07 (d, J=9.2 Hz, 1H), 5.76 (m, 1H), 5.18 (d, J=17.4 Hz, 1H), 5.14 (d, J=10.1 Hz, 1H), 4.34 (d, J=6.4 Hz, 1H), 3.91 (m, 1H), 3.10-0.86 (m, 38H) ppm. MS(ESI) m/z (%) 511 (MH+). HRMS calcd for $C_{31}H_{47}N_2O_4$ (MH+), 511.3536; found, 511.3550.

SMGP57: SMGP57 was synthesized according to the general procedure (II) described above using β-naloxamine, cyclohexanoic acid, BOP and DIEA in DCM followed by base hydrolysis. A white solid was obtained. Yield: 33%; $^1$H NMR (500 MHz, CDCl$_3$): δ 6.71 (d, J=8.1 Hz, 1H), 6.55 (d, J=8.0 Hz, 1H), 6.14 (d, J=9.1 Hz. 1H), 5.77 (m, 1H), 5.18 (d, J=17.4 Hz, 1H), 5.14 (d, J=10.0 Hz, 1H), 4.33 (d, J=6.1 Hz, 1H), 3.93 (m, 1H), 3.15-0.80 (m, 26H) ppm. $^{13}$C NMR (600 MHz, CDCl$_3$) δ 176.0, 143.1, 139.5, 135.3, 130.8, 124.7, 119.1, 118.0, 117.6, 93.7, 70.1, 62.5, 57.7, 49.7, 47.3, 45.7, 43.6, 31.3, 29.7, 29.6, 29.3, 25.8, 25.7, 23.6, 22.7 ppm. MS (ESI) m/z (%) 439 (MH+). HRMS calcd for $C_{26}H_{35}N_2O_4$(MH+), 439.2597; found, 439.2602.

SMGP58: SMGP58 was synthesized according to the general procedure (II) described above using β-naloxamine, 1-Adamantyl carboxylic acid, BOP and DIEA in DCM followed by base hydrolysis. A white solid was obtained. Yield: 26%; $^1$H NMR (500 MHz, CDCl$_3$) δ: 6.71 (d, J=8.2 Hz, 1H), 6.55 (d, J=8.2 Hz, 1H), 6.22 (d, J=9.5 Hz, 1H), 5.77 (m, 1H), 5.28 (s, 1H), 5.18 (d, J=17.2 Hz, 1H), 5.14 (d, J=10.2 Hz, 1H), 4.31 (d, J=5.9 Hz, 1H), 3.97 (m, 1H), 3.15-0.76 (m, 29H) ppm. MS (ESI) m/z (%) 491 (MH+). HRMS calcd for $C_{30}H_{39}N_2O_4$ (MH+), 491.2910; found, 491.2912.

The invention claimed is:

1. A compound of formula I:

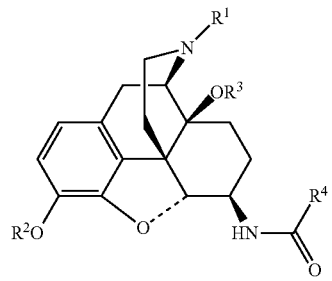

or a pharmaceutically acceptable salt thereof, wherein:
$R^1$ is allyl;
$R^2$ is hydrogen;
$R^3$ is hydrogen; and
$R^4$ is Ph-2I, Ph-H, Ph-4OC$_4$H$_9$, Ph-4CH$_2$-tButyl, Ph-4Si(OC$_2$H$_5$)$_3$, Ph-cHexane, PhCH$_2$Ph, PhOPh, Ph-Ph-Ph, or Ph-4-SCH$_3$.

2. The compound according to claim 1, wherein the compound is radiolabeled.

3. A pharmaceutical composition comprising a pharmaceutically acceptable carrier and a compound according to claim 1.

4. A method for reducing pain comprising administering to a subject suffering from pain a compound according to claim 1 in an amount effective to reduce pain.

5. The method according to claim 4, wherein pain is reduced without substantial reduction of intestinal motility.

6. The method according to claim 4, wherein pain is reduced without substantial respiratory depression.

7. The method of claim 4, wherein the subject suffering from pain is a μ-opioid-dependent patient.

8. A method for assaying for the kappa3 receptor comprising exposing a tissue to a compound according to claim 2, rinsing said tissue, and measuring the amount and/or location of said compound in said tissue.

9. A method for assaying for an opioid receptor comprising exposing a compound according to claim 2 to a source of receptor in vitro or in vivo, and measuring the amount and/or location of said compound bound to the receptor.

10. The compound according to claim 1, wherein $R^4$ is Ph-2I.

11. The compound according to claim 1, wherein $R^4$ is Ph-H.

12. The compound according to claim 1, wherein $R^4$ is Ph-4OC$_4$H$_9$.

13. The compound according to claim 1, wherein $R^4$ is Ph-4CH$_2$-tButyl.

14. The compound according to claim 1, wherein $R^4$ is Ph-4Si(OC$_2$H$_5$)$_3$.

15. The compound according to claim 1, wherein $R^4$ is Ph-cHexane.

16. The compound according to claim 1, wherein $R^4$ is PhCH$_2$Ph.

17. The compound according to claim 1, wherein $R^4$ is PhOPh.

18. The compound according to claim 1, wherein $R^4$ is Ph-Ph-Ph.

19. The compound according to claim 1, wherein $R^4$ is Ph-4-SCH$_3$.

20. The method according to claim 4, wherein $R^4$ is Ph-cHexane or Ph-4-SCH$_3$.

* * * * *